US012734114B2

(12) United States Patent
Su et al.

(10) Patent No.: US 12,734,114 B2
(45) Date of Patent: Sep. 15, 2026

(54) TWO-SECTION COMBINATION NASOGASTRIC TUBE

(71) Applicant: Chien-Chung Su, Taichung City (TW)

(72) Inventors: Chien-Chung Su, Taichung City (TW); Hsin-Liang Han, Taichung City (TW); Yu-Min Chang, Taichung City (TW); You-Ling Chih, Taichung City (TW)

(73) Assignee: Chien-Chung Su, Taichung City (TW)

( * ) Notice: Subject to any disclaimer, the term of this patent is extended or adjusted under 35 U.S.C. 154(b) by 663 days.

(21) Appl. No.: 18/323,705

(22) Filed: May 25, 2023

(65) Prior Publication Data

US 2024/0277581 A1 Aug. 22, 2024

(30) Foreign Application Priority Data

Feb. 21, 2023 (TW) ................................ 112106248

(51) Int. Cl.

| | |
|---|---|
| ***A61J 15/00*** | (2006.01) |
| ***A61M 39/08*** | (2006.01) |
| ***A61M 39/10*** | (2006.01) |
| ***A61M 39/20*** | (2006.01) |

(52) U.S. Cl.

CPC .......... *A61J 15/0003* (2013.01); *A61M 39/08* (2013.01); *A61M 39/1055* (2013.01); *A61M 39/20* (2013.01); *A61M 2039/1033* (2013.01)

(58) Field of Classification Search

CPC ................ A61J 15/0003; A61M 39/08; A61M 39/1055; A61M 39/20; A61M 2039/1033

See application file for complete search history.

(56) References Cited

U.S. PATENT DOCUMENTS

| | | | | |
|---|---|---|---|---|
| 5,694,978 A * | 12/1997 | Heilmann | ............. | A61M 39/20 138/89 |
| 9,504,630 B2 | 11/2016 | Liu | | |
| 2014/0088567 A1* | 3/2014 | Nieman | ................ | A61M 39/08 604/533 |
| 2014/0378907 A1* | 12/2014 | Liu | ..................... | A61J 15/0026 604/178 |
| 2020/0023176 A1* | 1/2020 | Hu | ......................... | A61B 5/153 |
| 2022/0362536 A1* | 11/2022 | Nguyen | ................ | A61F 5/4405 |

* cited by examiner

*Primary Examiner* — Dung T Ulsh
(74) *Attorney, Agent, or Firm* — MUNCY, GEISSLER, OLDS & LOWE, P.C.

(57) ABSTRACT

A two-section combination nasogastric tube includes an internal tube, an external tube, a joint, and a combining member. The internal tube has an inserting end and a mounting end. The inserting end is inserted into the human body through nasal cavity, with the mounting end left outside. The external tube has one end connected with a feeding port connector and the other end removably connected with the joint. The combining member is removably connected with the internal tube and the joint, and has a combining part and a screwing part. The combining part has a cone end. The mounting end is mounted around the combining part. The screwing part is screwed to the joint. According to the length requirement, the internal tube with an appropriate length is connected with the combining member, reducing the overall manufacturing process and cost, and improving the comfort of patient.

8 Claims, 11 Drawing Sheets

40

TWO-SECTION COMBINATION NASOGASTRIC TUBE

BACKGROUND OF THE INVENTION

1. Field of the Invention

The present invention relates to nasogastric tubes, and more particularly, to a two-section combination nasogastric tube whose internal tube and the external tube are detachable from the combining member.

2. Description of the Related Art

When a patient is unable to consume food on his/her own due to injury, illness or aging, the patient needs to be fed through a nasogastric tube, wherein the food is processed into a liquid state in advance and then fed into the stomach through the nasogastric tube for normally supplying the patient with calories and nutrition.

As disclosed by U.S. Pat. No. 9,504,630B2, a nasogastric tube is provided, comprising a connecting member which is provided with a flow channel passing therethrough and a first and a second connecting ends formed on two ends thereof. The first connecting end is connected to the first tube body through ultrasonic fusion or gluing. The second connecting end is provided with a positioning sleeve connected with the second tube body. The first tube body is placed in the human body, and the second tube body is connected with the feeding port connector, such that the liquid food is supplied from the second tube body to the first tube body via the connecting member, thereby normally supplying calories and nutrition to the patient.

However, during the manufacturing process of the aforementioned patent, the first tube body has to be combined with the connecting member through the ultrasonic fusion or gluing operations, which not only increase the complexity of the manufacturing process, but also increase the manufacturing cost.

Also, during the manufacturing process of the aforementioned patent, because one end of the first tube body is fixed to the connecting member, the length of the first tube body is therefore fixed in the manufacturing process. Therefore, during the actual usage, the length of the first tube body is not adjustable. To cope with the unchangeable length of the first tube body, the manufacturer produces different first tube bodies of different lengths.

When a patient needs to wear a nasogastric tube, medical staff or caregiver will visually measure the distance between the patient's nasal cavity and the stomach, and choose the first tube body having an appropriate length from several first tube bodies having fixed-lengths. However, the distance from the nasal cavity to the stomach is different for each patient. Therefore, it is necessary to insert the first tube body into the patient's stomach before determining if the length of the first tube body is suitable for the current patient. Based on the fact that the process of placing the first tube body is very uncomfortable, if the length of the first tube body is too short to reach into the stomach, it is necessary to pull out the first tube body first, and replace it with another first tube body having a different length, and then perform the tube placing process once more. As a result, the overall process causes serious distress and discomfort of the patient.

Therefore, in order to avoid that issue of the length of the first tube body being too short to reach into the patient's stomach, medical staff or caregiver will usually select the first tube body of a larger length. However, regarding the first tube body having an excessively longer size, the length exposed outside the nasal cavity will be longer as well, so that the excessive length of the first tube body has to be fixed on the patient's nose through adhesive tape, and the airtightness and sticky feeling of the adhesive tape easily cause discomfort of the patient.

SUMMARY OF THE INVENTION

To improve the issues above, the present invention provides a two-section combination nasogastric tube. According to the actual requirement of the patient, the internal tube with an appropriate length is combined with the combining member. The present invention not only simplifies the manufacturing process and reduces the cost thereof, but also improve the comfort of the patient by using the internal tube having the appropriate length.

For achieving the aforementioned objectives, the two-section combination nasogastric tube in accordance with an embodiment of the present invention comprises:

- an internal tube comprising an inserting end and an opposite mounting end, the inserting end configured to be placed into a human body through a nasal cavity of the human body, the mounting end configured to be arranged outside the nasal cavity of the human body;
- an external tube comprising a feeding end and an opposite connecting end, the feeding end being connected with a feeding port connector;
- a joint comprising a first joint part and an opposite second joint part, the first joint part being removably connected with the connecting end of the external tube, the second joint part comprising a rotatable thread ring; and
- a combining member removably connected between the internal tube and the joint, the combining member comprising a base part, a combining part, and a screwing part, the combining part and the screw part being disposed on opposite lateral sides of the base part, respectively, wherein an end part of the combining part is formed in a cone shape, the mounting end of the internal tube is mounted around the end part of the combining part, and the screwing part is screwedly combined with the thread ring of the second joint part.

In an embodiment, the combining member comprises a channel passing through the base part, the combining part, and the screwing part, and in communication with the internal tube, the external tube, and the joint. The channel comprises a first channel section and a second channel section. The first channel section is positionally aligned with the combining part and a portion of the base part. The second channel section is positionally aligned with the screwing part and a portion of the base part. Normally, the first channel section is not in communication with the second channel section.

In an embodiment, a non-return film is disposed between the first channel section and the second channel section. The non-return film comprises a crevice, which is normally sealed. An end part of the second joint part protrudes from the thread ring. When the screwing part is screwed to the thread ring of the joint, the end part of the second joint part breaks through the crevice, such that the first channel section is in communication with the second channel section.

In an embodiment, the inner diameter of the first channel section is smaller than the inner diameter of the second channel section.

In an embodiment, the combining member further comprises a closing part, which is connected to the outer periphery of the base part. The closing part is allowed to be bendable to close the channel from the screwing part.

In an embodiment, the closing part comprises an extension section and a plug. An end of the extension section is connected to the outer periphery of the base part, and the plug is disposed on the same lateral side with the screwing part and arranged on another end of the extension section, so as to protrude thereon to plug an end opening of the channel.

In an embodiment, the combining part comprises a first body section and a second body section. The first body section is connected between the base part and the second body section. The second body section is approximately formed in a cone shape. The first body section comprises a ring-shaped protrusion block, and the outer diameter of the protrusion block is larger than the maximum outer diameter of the second body section.

In an embodiment, the second body section tapers from one end thereof connected with the first body section toward a direction away from the base part.

In an embodiment, the second body section comprises a plurality of retaining grooves concavely formed on the outer surface thereof.

In an embodiment, the base part comprises a first face and an opposite second face. The combining part is connected with the first face, and the screwing part is connected with the second face. The first face of the base part comprises two symmetrical grip parts protruding thereon, with the combining part arranged between the two grip parts.

With such configuration, according to the length requirement of the internal tube for the patient, the internal tube with an appropriate length is combined with the combining member. Therefore, the ultrasonic fusion or gluing operations are saved, so as to simplify the manufacturing process and reduce the cost of manufacturing.

Also, after the internal tube is inserted into the stomach of the patient, the exposed portion is cut for an appropriate length to be left outside, so as to form the mounting end of the internal tube, and the mounting end is then combined with the combining member, thereby directly providing the internal tube having an appropriate length for the patient, preventing the issue of inappropriate length of the internal tube. Therefore, it is unnecessary to repeat the tube insertion process or adhere the excessive tube body on the nose of the patient, which cause the discomfort of the patient. Thus, the present invention effectively improves the comfort of usage for the patient.

In addition, during the process of mounting the internal tube on the combining member, the cone-shaped combining part having the smaller outer diameter is efficiently positioned and connected with the internal tube, shortening the mounting duration of the internal tube and the combining member. When the internal tube is mounted around the protrusion block, the protrusion block and the diameter difference between the first body section and the second body section provide an engagement effect, preventing the detachment of the internal tube from the combining member.

DETAILED DESCRIPTION OF THE INVENTION

Figure 1:
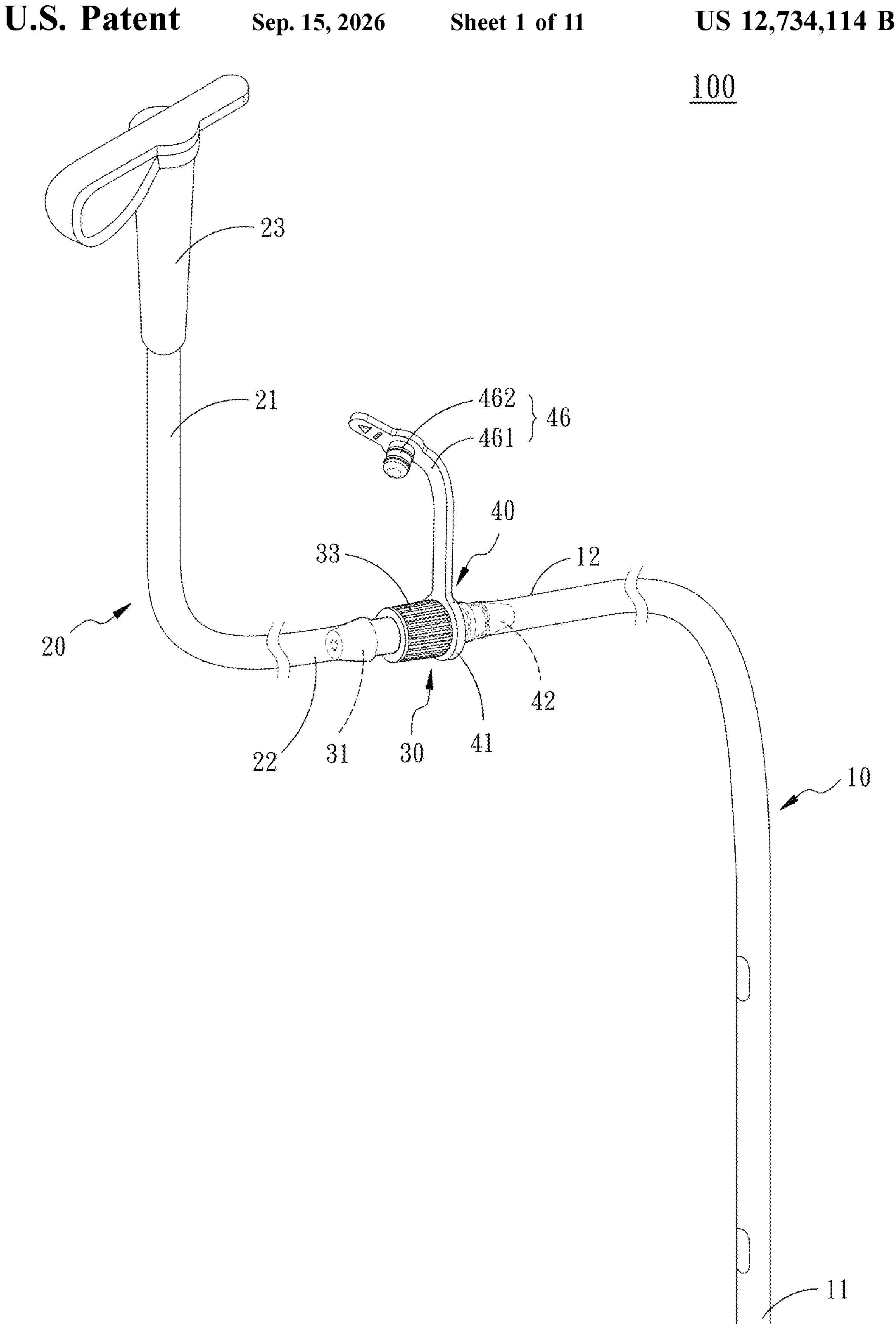
FIG. 1 is a perspective view of the first embodiment of the present invention.

The aforementioned and further advantages and features of the present invention will be understood by reference to the description of the preferred embodiment in conjunction with the accompanying drawings where the components are illustrated based on a proportion for explanation but not subject to the actual component proportion.

The directional terms of, for example, "up", "down", "front", "rear", "left", "right", "inner", "outer", and "side" are only used herein for illustrating the relative directions shown in the drawings. Therefore, the directional terms are applied for the purpose of illustration and understanding of the present invention, instead of limiting the present invention.

Referring to FIG. 1 to FIG. 7, a two-section combination nasogastric tube 100 in accordance with the first embodiment of the present invention is disclosed, comprising an internal tube 10, an external tube 20, a joint 30, and a combining member 40.

Figure 7:
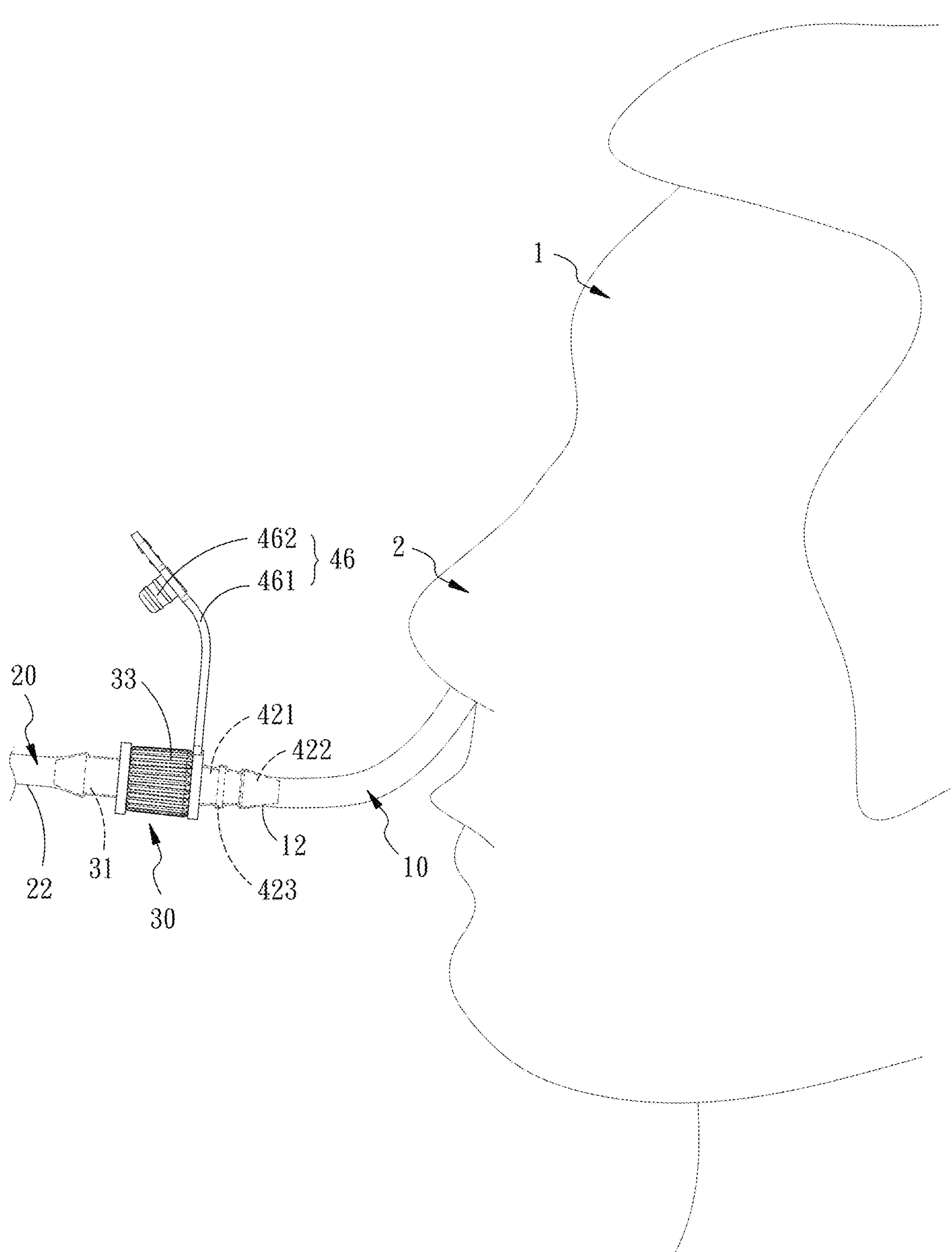
FIG. 7 is a schematic view illustrating the present invention worn by a patient.

The internal tube 10 comprises an inserting end 11 and a mounting end 12 in opposite to the inserting end 11. The inserting end 11 is allowed to be placed into the stomach (not shown) of the human body (patient 1) from the nasal cavity 2 of the human body (patient 1), and the mounting end 12 is left outside the nasal cavity 2 of the human body, as shown by FIG. 7.

Notably, the length of the internal tube 10 is able to be decided according to the requirement of the patient 1. In other words, when the inserting end 11 of the internal tube 10 is placed into the stomach of the patient 1 from the nasal cavity 2 of the patient 1, a portion of the internal tube 10 exposed outside is cut at an appropriate length, so as to form a mounting end 12 of the internal tube 10. In the present invention, the length of the internal tube 10 is not limited.

Figure 2:
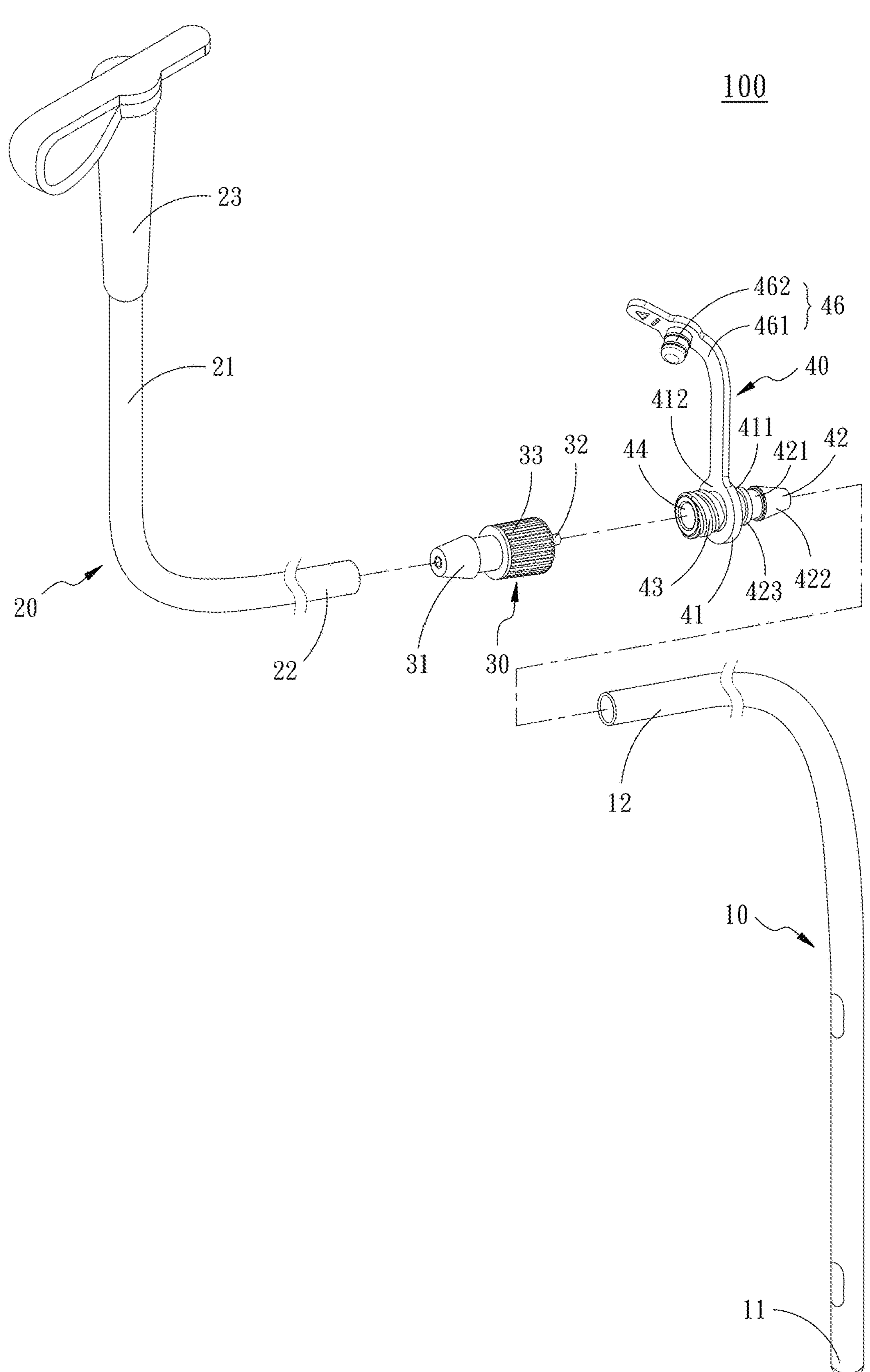
FIG. 2 is an exploded view of the first embodiment of the present invention.

The external tube 20 comprises a feeding end 21 and a connecting end 22 in opposite to the feeding end 21. The feeding end 21 is connected with a feeding portion connector 23, so that a liquid food is able to be input into the external tube 20 from the feeding port connector 23, as shown by FIG. 1 and FIG. 2.

Figure 3:
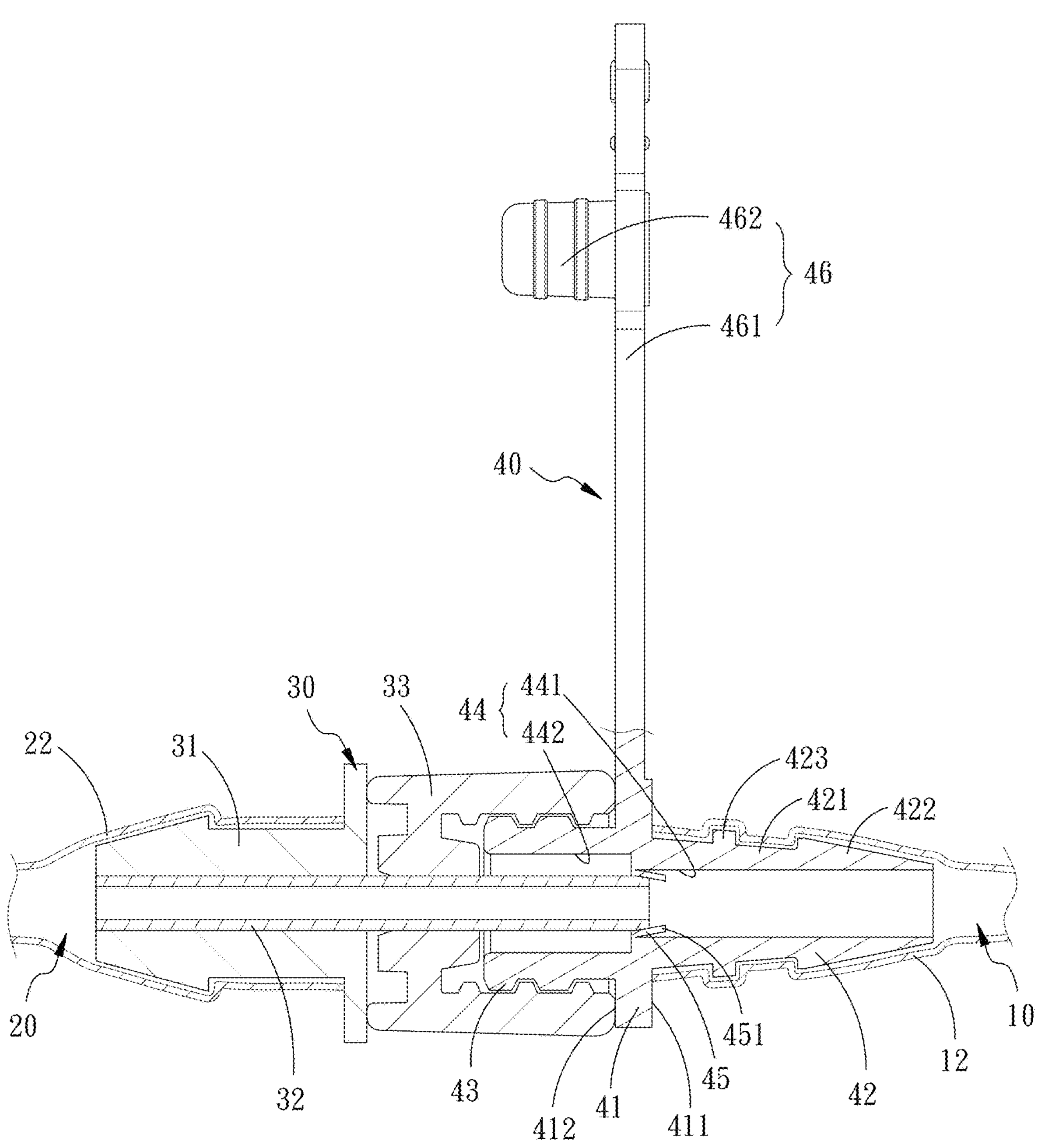
FIG. 3 is a partially sectional view of the first embodiment of the present invention.

The joint 30 comprises a first joint part 31 and a second joint part 32 in opposite to the first joint part 31. The first joint part 31 of the joint 30 is removably connected with the connecting end 22 of the external tube 20, and the joint 30 is in communication with the external tube 20. The second joint part 32 comprises a rotatable thread ring 33. The inner periphery of the thread ring 33 is provided with a thread. Therein, an end part of the second joint part 32 protrudes out of the thread ring 33, as shown by FIG. 2 and FIG. 3. In the embodiment, the joint 30 is a Luer taper.

The combining member 40 is removably connected between the internal tube 10 and the joint 30. The combining member 40 comprises a base part 41, a combining part 42, and a screwing part 43. Therein, the base part 41 is approximately formed in a column shape. The base part 41 comprises a first face 411 and a second face 412 in opposite to the first face 411. The combining part 42 is connected with the first face 411, and the screwing part 43 is connected with the second face 412. The mounting end 12 of the internal tube 10 is mounted around the combining part 42. The joint 30 is screwedly combined with the screwing part 43.

The combining part 42 comprises a first body section 421 and a second body section 422. The first body section 421 is connected between the base part 41 and the second body section 422. The second body section 422 is approximately formed in a cone shape. The first body section 421 tapers from its one end connected with the base part 41 toward the second body section 422. The second body section 422 tapers from its one end connected with the first body section 421 toward the direction away from the base part 41. In the embodiment, the largest outer diameter of the first body section 421 is equal to the largest outer diameter of the second body section 422. The smallest outer diameter of the first body section 421 is larger than the smallest outer diameter of the second body section 422.

Figure 4:
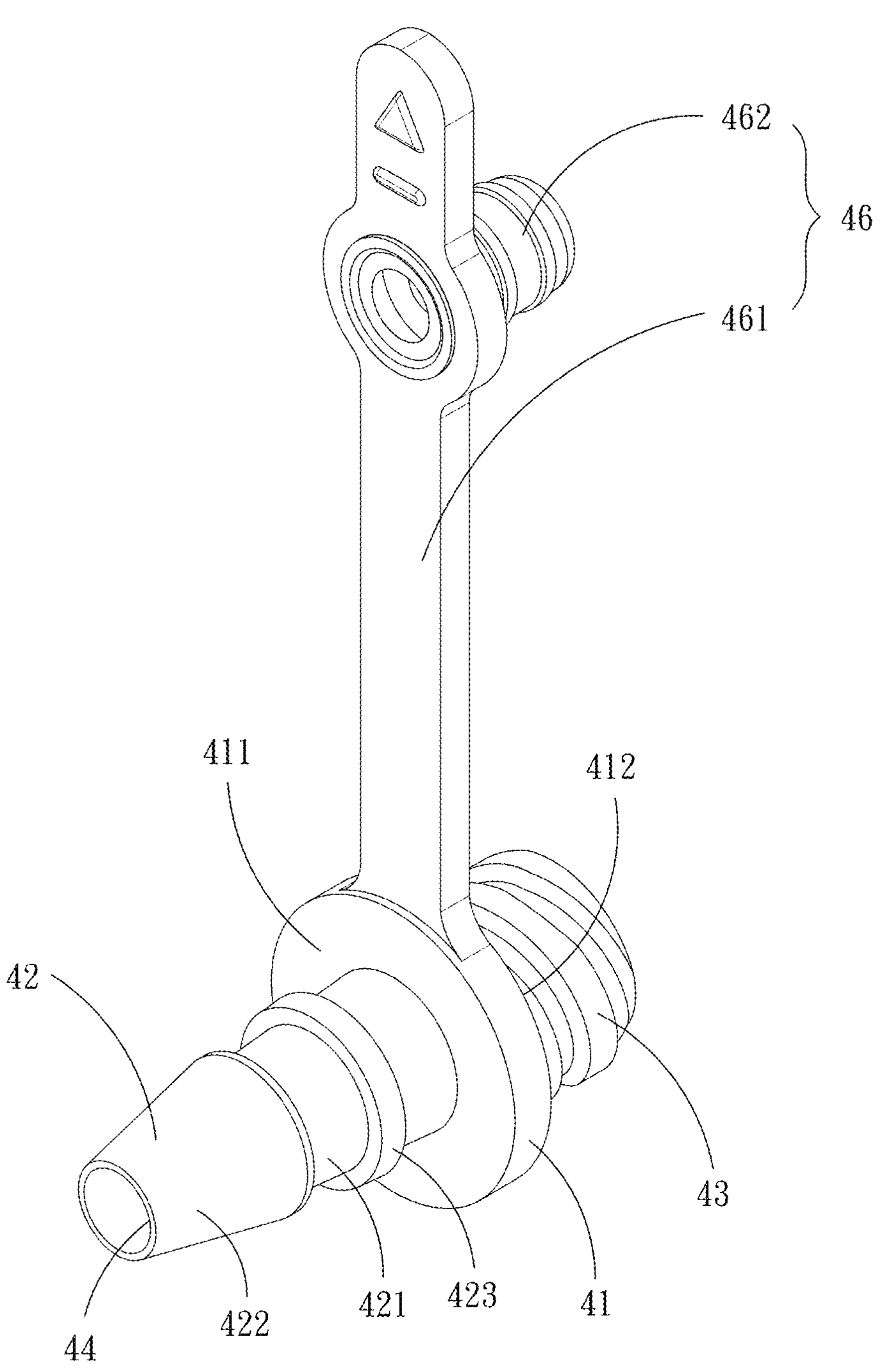
FIG. 4 is a perspective view of the combining member of the first embodiment of the present invention.
Figure 6:
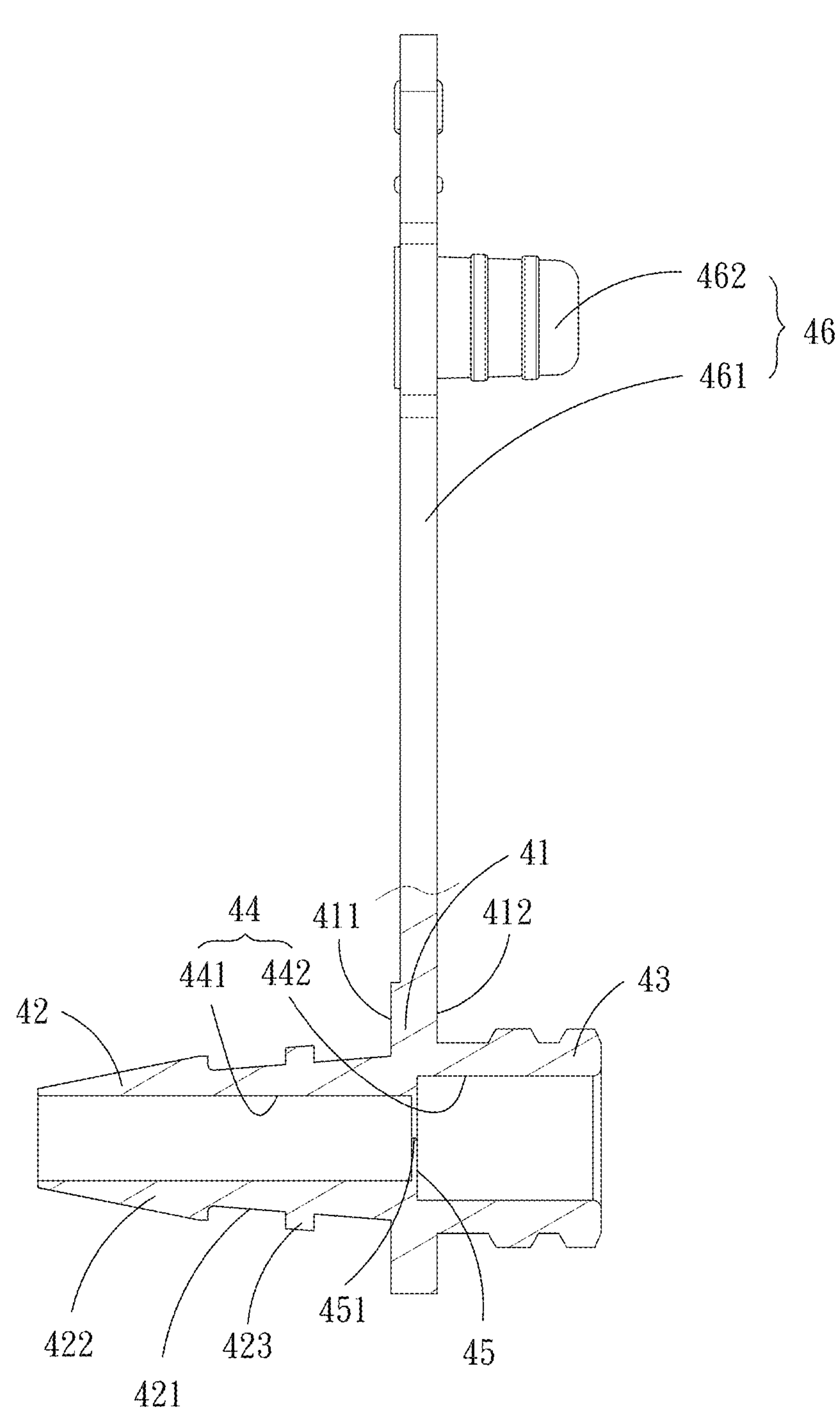
FIG. 6 is a partially sectional view of the combining member of the first embodiment of the present invention.

Also, the first body section 421 comprises a ring-shaped protrusion block 423 disposed at the middle section thereof, and the outer diameter of the protrusion block 423 is larger than the largest outer diameter of the second body section 422, as shown by FIG. 3, FIG. 4, and FIG. 6. In the embodiment, the outer diameter of the protrusion block 423 is larger than the largest outer diameter of the first body section 421.

The screwing part 43 comprises a thread formed on the outer periphery thereof. The screwing part 43 is able to be screwedly combined with the thread ring 33 of the second joint part 32 of the joint 30, as shown by FIG. 2 and FIG. 3.

The combining member 40 comprises a channel 44 passing through the base part 41, the combining part 42, and the screwing part 43, and in communication with the internal tube 10, the external tube 20, and the joint 30. The channel 44 comprises a first channel section 441 and a second channel section 442. The first channel section 441 is in positional alignment with the combining part 42 and a portion of the base part 41. The second channel section 442 is in positional alignment with the screwing part 43 and a portion of the base part 41. Normally, the first channel section 441 is not in communication with the second channel section 442. Therein, the inner diameter of the first channel section 441 is smaller than the inner diameter of the second channel section 442.

Figure 5:
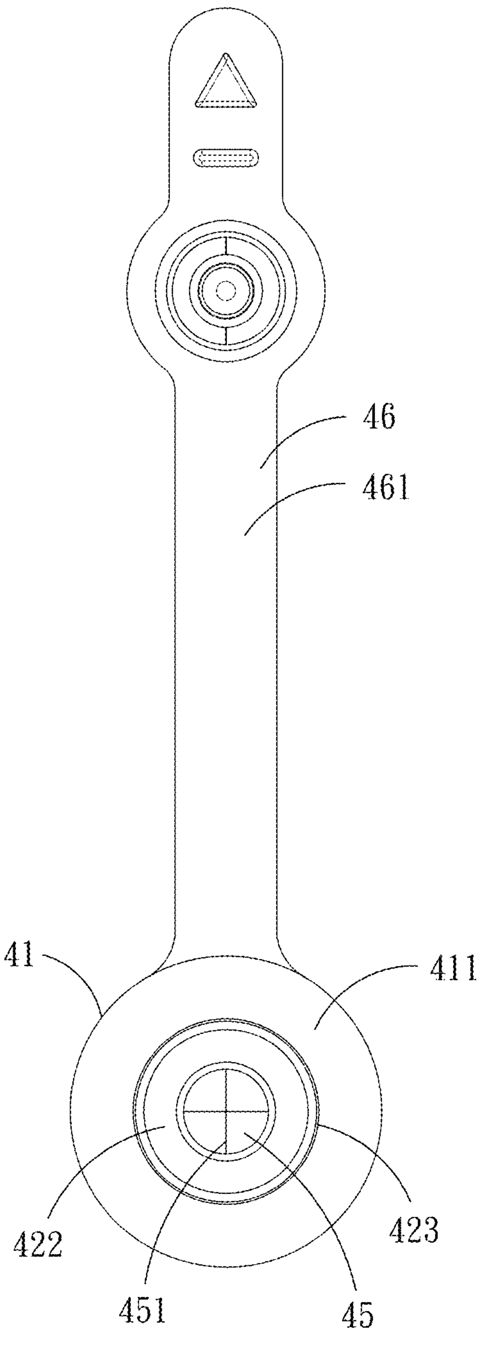
FIG. 5 is a front view of the combining member of the first embodiment of the present invention.

Further, referring to FIG. 3, FIG. 5 and FIG. 6, a non-return film 45 is disposed between the first channel section 441 and the second channel section 442. The non-return film 45 comprises a crevice 451, which is normally sealed. When the screwing part 43 is screwed to the thread ring 33 of the joint 30, an end part of the second joint part 32 breaks through the crevice 451, whereby the first channel section 441 is in communication with the second channel section 442. In the embodiment, the non-return film 45 is integrally formed with the combining member 40.

In addition, the combining member 40 further comprises a closing part 46 connected to the outer periphery of the base part 41. The closing part 46 is allowed to be bent to close the channel 44 from the screwing part 43. Therein, the closing part 46 comprises an extension section 461 and a plug 462. An end of the extension section 461 is connected to the outer periphery of the base part 41, and the plug 462 is disposed on another end of the extension section 461 and arranged on the same lateral side (extending from the second face 412) with the screwing part 43, so as to tightly protrude thereon to plug the end opening of the channel 44 corresponding to the screwing part 43. When the external tube 20 and the joint 30 are removed from the combining member 40, to prevent the channel 44 of the combining member 40 and the internal tube 10 from pollution of external environment, the extension section 461 of the closing part 46 is able to be bent, and the plug 462 is used to plug the end opening of the channel 44 of the screwing part 43, such that the channel 44 of the combining member 40 and the internal tube 10 are isolated from the external environment.

Figure 8:
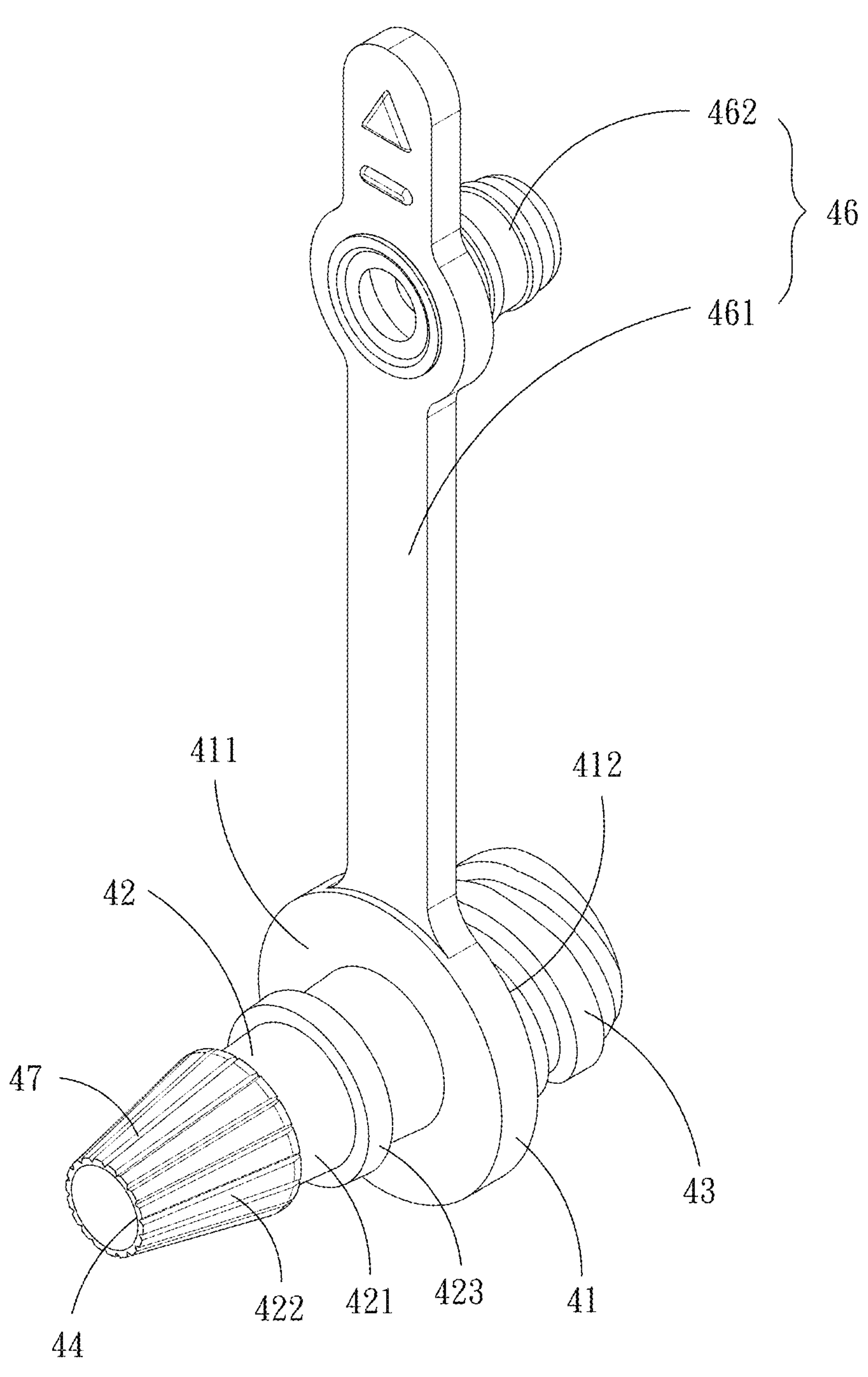
FIG. 8 is a perspective view of the combining member of the second embodiment of the present invention.

Referring to FIG. 8 showing the second embodiment, compared with the first embodiment, the difference lies in that the second body section 422 of the combining part 42 comprises a plurality of retaining grooves 47 concavely formed on the outer surface thereof, wherein the length direction of each retaining groove 47 is the same as the inclination direction of the taper of the second body section 422, and each retaining groove 47 increases the frictional force generated between the second body section 422 and the mounting end 12 of the internal tube 10, so as to achieve the retaining effect between the internal tube 10 and the combining member 40.

Figure 9:
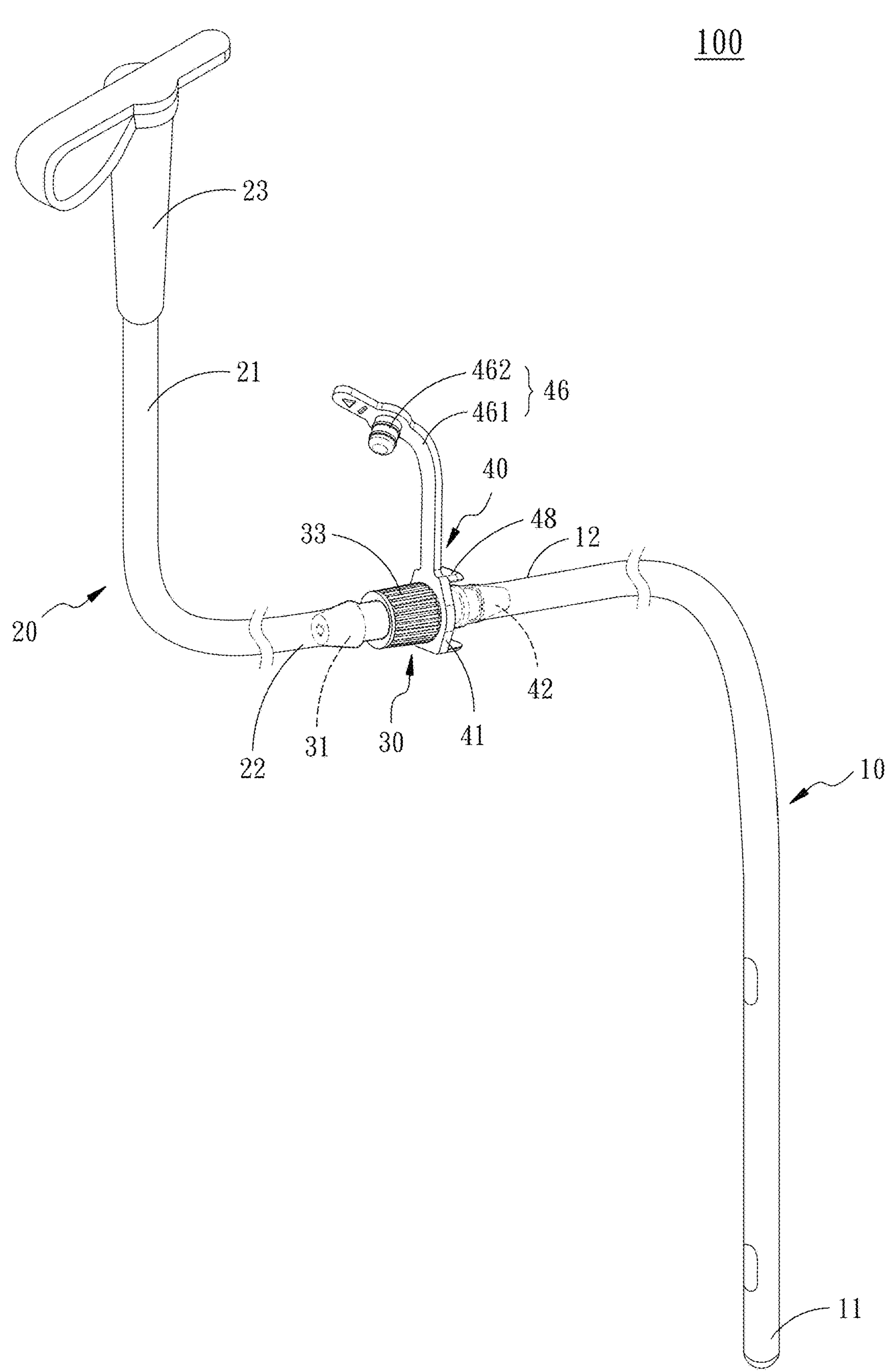
FIG. 9 is a perspective view of the third embodiment of the present invention.
Figure 10:
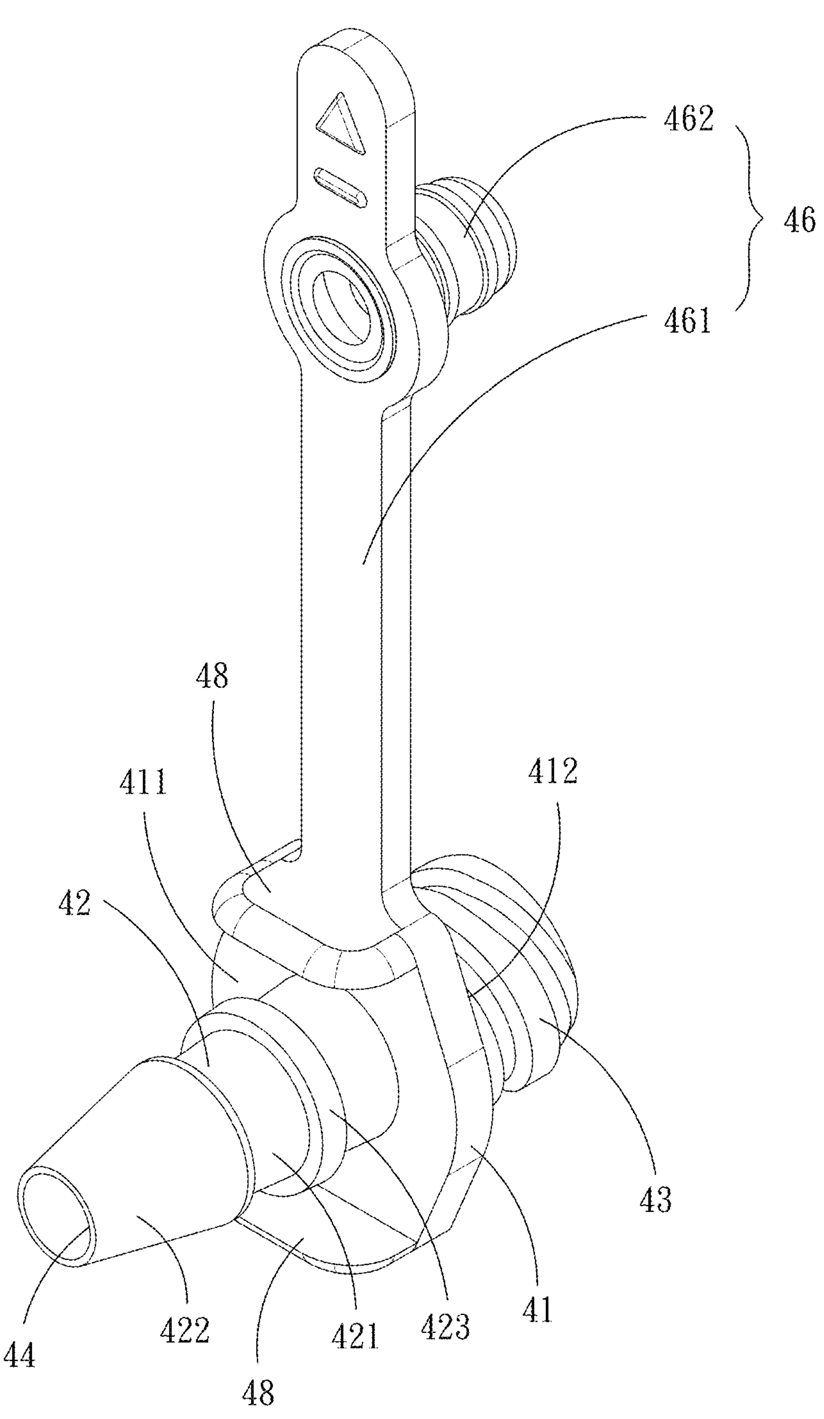
FIG. 10 is a perspective view of the combining member of the third embodiment of the present invention.

Referring to FIG. 9 to FIG. 10, showing the third embodiment, compared with the first embodiment, the difference lies in that the first face 411 of the base part 41 of the combining member 40 comprises two symmetrical grip parts 48, with the combining part 42 arranged between the two grip parts 48. The two grip parts 48 are approximately formed in a rectangular shape, so that the two grip parts 48 are applied for the thumb and the forefinger of the user to clamp and hold steady the combining member 40, so as to combine the combining member 40 with the internal tube 10 or use the plug 462 of the closing part 46 to tightly plug the end opening of the channel 44 of the screw part 43.

Figure 11:
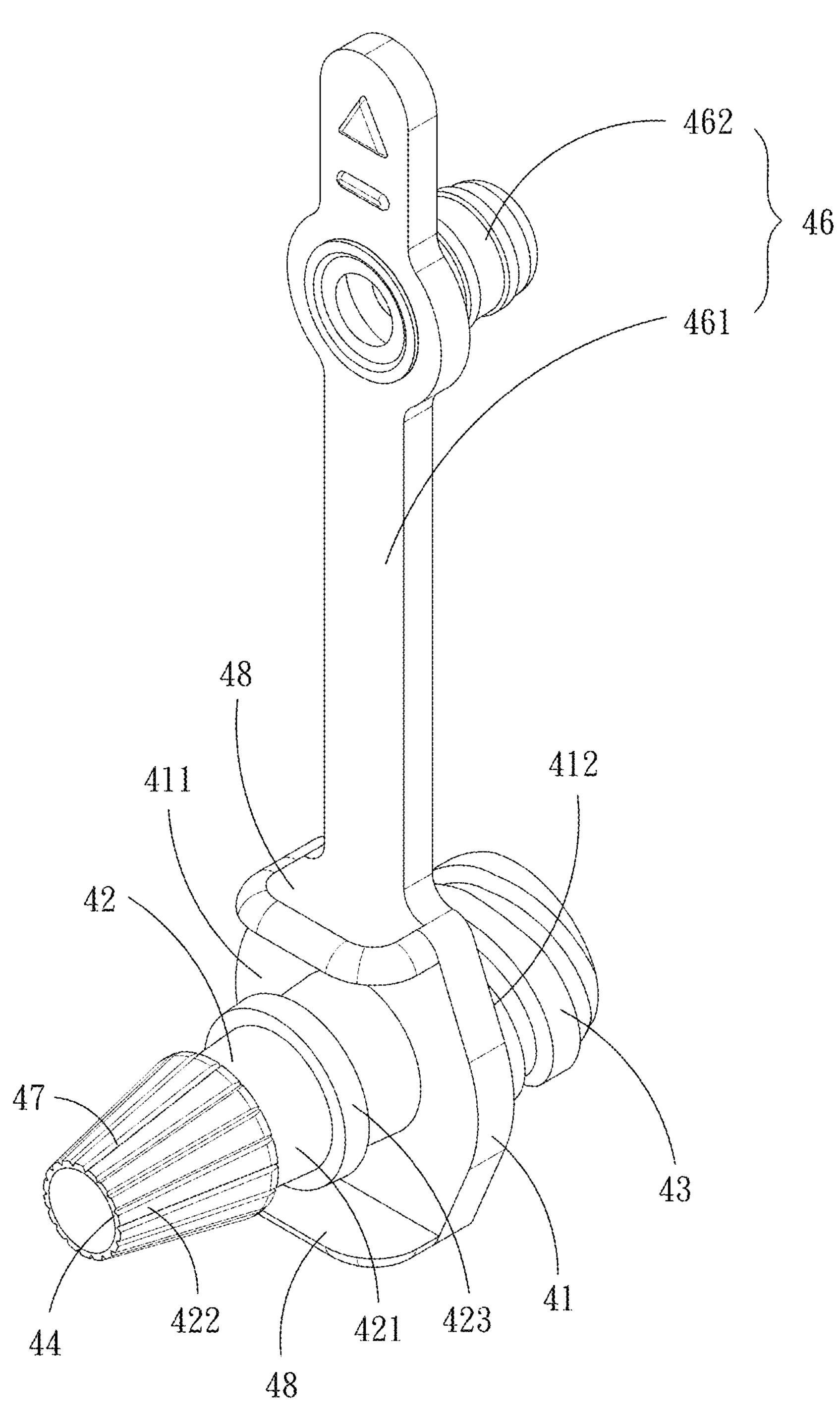
FIG. 11 is a perspective view of the combining member of the fourth embodiment of the present invention.

Referring to FIG. 11 showing the fourth embodiment, compared with the third embodiment, the difference lies in that the second body section 422 of the combining part 42 comprises a plurality of retaining grooves 47 concavely formed on the outer surface thereof, wherein the length direction of each retaining groove 47 is the same as the inclination direction of the taper of the second body section 422, and each retaining groove 47 increases the frictional force generated between the second body section 422 and the mounting end 12 of the internal tube 10, so as to achieve the retaining effect between the internal tube 10 and the combining member 40.

Referring to FIG. 1, FIG. 3, and FIG. 7, when the patient 1 need to assemble the two-section combination nasogastric tube 100, the external tube 20 is connected with the feeding port connector 23 and the joint 30, respectively, then the inserting end 11 of the internal tube 10 is inserted into the stomach of the patient 1 from the nasal cavity 2 of the patient 1. Then, a portion of the internal tube 10 exposed outside the nasal cavity 2 is cut at an appropriate length, so as to form the mounting end 12 of the internal tube 10. Next, the mounting end 12 of the internal tube 10 is mounted around the combining part 42 of the combining member 40. Finally, the joint 30 combined with the external tube 20 is screwedly combined with the screwing part 43 of the combining member 40. Thus, the two-section combination nasogastric tube 100 is worn on the patient 1.

With the foregoing configuration, the present invention achieves following advantages.

The two-section combination nasogastric tube 100 of the present invention, based on the length requirement of the patient 1, has the internal tube 10 with an appropriate length combined with the combining member 40, so as to omit the ultrasonic fusion or gluing operations during the manufacturing process, thereby simplifying the overall manufacturing process and reducing the cost of manufacturing.

After the internal tube 10 is inserted into the stomach of the patient 1, an appropriate length of the exposed section is cut, so as to form the mounting end 12 of the internal tube 10, which is combined with the combining member 40. Therefore, the present invention directly provides the internal tube 10 having an appropriate length for the patient 1. Therefore, it is unnecessary to repeat the tube insertion process or adhere the excessive tube body on the nose of the patient 1, which cause the discomfort of the patient. Thus, the present invention effectively improves the comfort of usage for the patient 1.

During the process of mounting the internal tube 10 on the combining member 40, the cone-shaped combining part 42 having the smaller outer diameter is efficiently positioned and connected with the internal tube 10, shortening the mounting duration of the internal tube 10 and the combining member 40. When the internal tube 10 is mounted around the protrusion block 423, the protrusion block 423 and the diameter difference between the first body section 421 and the second body section 422 provide an engagement effect, preventing the detachment of the internal tube 10 from the combining member 40.

When there is no need to provide the liquid food, the closing part 46 integrally formed with the combining member 40 closes the end opening of the channel 44 of the screwing part 43, so as to isolate the channel 44 of the combining member 40 and the internal tube 10 from the external environment. Therefore, the channel 44 of the combining member 40 and the internal tube 10 are prevented from the pollution of the external environment.

Although particular embodiments of the invention have been described in detail for purposes of illustration, various modifications and enhancements may be made without departing from the spirit and scope of the invention. Accordingly, the invention is not to be limited except as by the appended claims.

What is claimed is:

1. A two-section combination nasogastric tube, comprising:

an internal tube comprising an inserting end and an opposite mounting end, the inserting end configured to be placed into a human body through a nasal cavity of the human body, the mounting end configured to be arranged outside the nasal cavity of the human body;

an external tube comprising a feeding end and an opposite connecting end, the feeding end being connected with a feeding port connector;

a joint comprising a first joint part and an opposite second joint part, the first joint part being removably connected with the connecting end of the external tube, the second joint part comprising a rotatable thread ring; and a combining member removably connected between the internal tube and the joint, the combining member comprising a base part, a combining part, and a screwing part, the combining part and the screw part being disposed on opposite lateral sides of the base part, respectively, wherein an end part of the combining part is formed in a cone shape, the mounting end of the internal tube is mounted around the end part of the combining part, the combining part comprises a first body section and a second body section; the first body section is connected between the base part and the second body section; the second body section is formed in a cone shape; the first body section comprises a ring-shaped protrusion block, and an outer diameter of the protrusion block is larger than a maximum outer diameter of the second body section, the second body section comprises a plurality of retaining grooves concavely formed on an outer surface thereof, and the screwing part is screwedly combined with the thread ring of the second joint part.

2. The two-section combination nasogastric tube of claim 1, wherein the combining member comprises a channel passing through the base part, the combining part, and the screwing part, and the channel is in communication with the internal tube, the external tube, and the joint; the channel comprises a first channel section and a second channel section; the first channel section is positionally aligned with the combining part and a portion of the base part; the second channel section is positionally aligned with the screwing part and a portion of the base part; normally, the first channel section is not in communication with the second channel section.

3. The two-section combination nasogastric tube of claim 2, wherein a non-return film is disposed between the first channel section and the second channel section; the non-return film comprises a crevice, which is normally sealed; an end part of the second joint part protrudes from the thread ring; when the screwing part is screwed to the thread ring of the joint, the end part of the second joint part breaks through the crevice, such that the first channel section is in communication with the second channel section.

4. The two-section combination nasogastric tube of claim 2, wherein an inner diameter of the first channel section is smaller than an inner diameter of the second channel section.

5. The two-section combination nasogastric tube of claim 2, wherein the combining member further comprises a closing part, which is connected to an outer periphery of the base part; the closing part is bendable to close the channel from the screwing part.

6. The two-section combination nasogastric tube of claim 5, wherein the closing part comprises an extension section and a plug; an end of the extension section is connected to the outer periphery of the base part, and the plug is disposed on a same lateral side with the screwing part and arranged on another end of the extension section, so as to protrude thereon to tightly plug an end opening of the channel.

7. The two-section combination nasogastric tube of claim 1, wherein the second body section tapers from one end thereof connected with the first body section toward a direction away from the base part.

8. The two-section combination nasogastric tube of claim 1, wherein the base part comprises a first face and an opposite second face; the combining part is connected with the first face, and the screwing part is connected with the second face; the first face of the base part comprises two symmetrical grip parts protruding thereon, with the combining part arranged between the two grip parts.

* * * * *